United States Patent
Pleschke et al.

(10) Patent No.: US 7,259,267 B2
(45) Date of Patent: Aug. 21, 2007

(54) DIFLUOROBENZO-1,3-DIOXOLES

(75) Inventors: Axel Pleschke, Köln (DE); Albrecht Marhold, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 119 days.

(21) Appl. No.: 11/126,534

(22) Filed: May 11, 2005

(65) Prior Publication Data

US 2005/0272811 A1 Dec. 8, 2005

(30) Foreign Application Priority Data

May 14, 2004 (DE) .................. 10 2004 024 011

(51) Int. Cl.
*C07D 317/44* (2006.01)

(52) U.S. Cl. ...................... 549/437; 549/439

(58) Field of Classification Search ............... 549/439, 549/437

See application file for complete search history.

(56) References Cited

U.S. PATENT DOCUMENTS

| 4,536,587 A | 8/1985 | Sirrenberg et al. | 549/366 |
| 4,743,611 A | 5/1988 | Malamas et al. | 514/390 |
| 5,070,098 A | 12/1991 | Fuchs et al. | 514/359 |
| 5,260,460 A | 11/1993 | Andres et al. | 549/362 |
| 5,663,189 A | 9/1997 | Maurer et al. | 514/397 |
| 2004/0116417 A1 | 6/2004 | Bouble et al. | 514/227.8 |

FOREIGN PATENT DOCUMENTS

| DE | 28 48 531 | 6/1980 |
| WO | 02/081453 | 10/2002 |

*Primary Examiner*—Amelia A. Owens
(74) *Attorney, Agent, or Firm*—Michael A. Miller

(57) ABSTRACT

The invention relates to difluorobenzo-1,3-dioxoles, to a process for their preparation, and to their use for preparing medicaments and crop protection agents.

9 Claims, No Drawings

DIFLUOROBENZO-1,3-DIOXOLES

The invention relates to difluorobenzo-1,3-dioxoles, to a process for their preparation, and to their use for preparing medicaments and crop protection agents.

Difluorobenzo-1,3-dioxoles are valuable building blocks in active agrochemical and pharmaceutical ingredients; see also WO 02/81453, in particular example 321. In order to be able to introduce the difluorobenzo-1,3-dioxole building block into the active ingredient molecule, 5-bromodifluorobenzo-1,3-dioxole is subjected to a palladium-catalysed transformation which is expensive from an industrial viewpoint. There is therefore a need to provide difluorobenzo-1,3-dioxoles which can be incorporated in a simple manner into such active ingredient molecules via a functionality intrinsic to them and which can be prepared in a simple and efficient process.

Compounds of the formula (I) have now been found

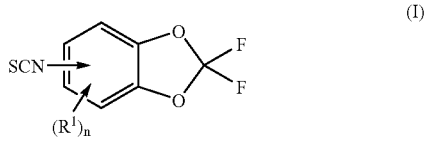

(I)

in which
$R^1$ is $C_1$-$C_{12}$-alkyl, $C_1$-$C_{12}$-fluoroalkyl, $C_1$-$C_{12}$-alkoxy, $C_1$-$C_{12}$-fluoroalkoxy, cyano, nitro, iodine, bromine, chlorine or fluorine and
n is 0, 1, 2 or 3.

The compounds of the formula (I) can be converted in a simple manner known from WO 02/81453 to the thioxoimidazolinones described there.

A process has also been found for preparing compounds of the formula (I), which is characterized in that compounds of the formula (II)

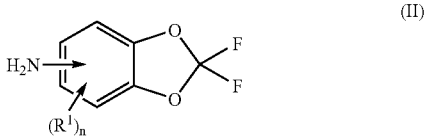

(II)

in which $R^1$ and n are each as defined above are converted in a manner known in principle to the corresponding isothiocyanates.

Preferred processes include:
The reaction with thiophosgene or other thiocarbamic acid derivatives, in particular chlorothiocarbonylimidazole or thiocarbonylbisimidazole or
the reaction with carbon disulphide in the presence of alkali metal base and subsequently the reaction either with an oxidizing agent or with phosgene or oxalyl chloride or
the preparation of corresponding isonitriles or isocyanide dihalides and subsequent sulphurization.

The reaction with thiophosgene is particularly preferred, and the reaction is advantageously effected in aqueous-acidic medium.

The processes mentioned are sufficiently well known in terms of principle from the literature. The compounds of the formula (II) used as starting compounds are either known from the literature or can be prepared analogously to the literature. It is to be regarded as particularly surprising that the difluorobenzodioxole function which is known to be labile and thermally sensitive and sensitive towards halogen exchange is not attacked to a significant extent by the reaction.

The scope of the invention embraces all radical definitions, parameters and illustrations above and listed hereinbelow, in general or within areas of preference, in any combination with one another, i.e. also between the particular areas and areas of preference.

Alkyl and alkoxy are each independently a straight-chain, cyclic, branched or unbranched alkyl and alkoxy radical respectively, and the radicals mentioned may optionally be further substituted by $C_1$-$C_4$-alkoxy radicals.

$C_1$-$C_{12}$-Alkyl is, for example and with preference, methyl, ethyl, n-propyl, isopropyl, n-butyl, sec-butyl, tert-butyl, n-pentyl, 1-methylbutyl, 2-methylbutyl, 3-methylbutyl, neopentyl, 1-ethylpropyl, cyclohexyl, cyclopentyl, n-hexyl, n-heptyl, n-octyl, n-decyl and n-dodecyl.

$C_1$-$C_{12}$-Alkoxy is, for example and with preference, methoxy, ethoxy, n-propoxy, isopropoxy, n-butoxy, sec-butoxy, tert-butoxy, n-pentoxy, cyclohexoxy, cyclopentoxy, n-hexoxy, n-heptoxy, n-octoxy, n-decoxy and n-dodecoxy Fluoroalkyl and fluoroalkoxy are in each case independently a straight-chain, cyclic, branched or unbranched alkyl radical and alkoxy radical respectively, each of which is substituted singly, multiply or fully by fluorine atoms.

For example, $C_1$-$C_{12}$-fluoroalkyl is trifluoromethyl, 2,2,2-trifluoroethyl, pentafluoroethyl, nonafluorobutyl, heptafluoroisopropyl, perfluorooctyl and perfluorododecyl.

For example, $C_1$-$C_{12}$-fluoroalkoxy is trifluoromethoxy, 2,2,2-trifluoroethoxy, pentafluoroethoxy, nonafluorobutoxy, heptafluoroisopropoxy, perfluorooctoxy and perfluorododecoxy.

The preferred substitution patterns for the compounds of the formulae (I) and (II) are defined hereinbelow:
$R^1$ is more preferably methyl, ethyl, n-propyl, chlorine, fluorine and bromine, most preferably chlorine or fluorine.
n is preferably 0, 1 or 2, more preferably 0 or 1 and most preferably 0.

A particularly preferred compound of the formula (I) is 5-isothiocyanato-2,2-difluorobenzo-1,3-dioxole.

A particularly preferred compound of the formula (II) is 5-amino-2,2-difluorobenzo-1,3-dioxole.

The inventive compounds of the formula (I) are suitable in particular for preparing pharmaceuticals, medicines, agrochemicals or intermediates thereof. Compounds of the formula (I) may be used preferably for the preparation of thioxoimidazolinones, in particular for those such as are described in WO 02/81453.

EXAMPLES

Example 1

Preparation of 5-isothiocyanato-2,2-difluorobenzo[1,3]-dioxole:

34.6 g of 5-amino-2,2-difluorobenzodioxole were added dropwise to a solution of 90 ml of conc. hydrochloric acid in 350 ml of water. The mixture was stirred for a further 30 minutes and then 27 g of thiophosgene were metered in rapidly. The mixture was stirred at the given temperature for a further 3 hours, the almost colourless suspension was admixed with 150 ml of dichloromethane and the dichloromethane was removed. The crude product was distilled at 45 mbar. 28 g (=89% of theory) were obtained as a colourless to yellowish liquid.

Boiling point: 136° C./45 mbar.

$^1$H NMR (400 MHz, CDCl$_6$): 6.96 (m, 2H), 7.02 (m, 1H)

The invention claimed is:

1. A compound of the formula (I),

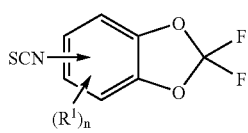

wherein
R$^1$ is C$_1$-C$_{12}$-alkyl, C$_1$-C$_{12}$-fluoroalkyl, C$_1$-C$_{12}$-alkoxy, C$_1$-C$_{12}$-fluoroalkoxy, cyano, nitro, iodine, bromine, chlorine or fluorine and
n is 0, 1, 2 or 3.

2. The compound according to claim 1, wherein the compound is 5-isothiocyanato-2,2-difluorobenzo-1,3-dioxole (n is 0).

3. A process for preparing compounds according to claim 1 comprising reacting compounds conforming structurally to the formula (II)

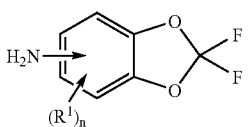

wherein R$^1$ and n are defined as in claim 1,
with thiophosgene in the presence of an aqueous-acidic medium thereby forming isothiocyanates corresponding structurally to the formula (I) as set forth in claim 1.

4. The process according to claim 3, wherein the compound conforming structurally to the formula (II) is 5-amino-2,2-difluorobenzo-1,3-dioxole (n is 0).

5. A process for preparing isothiocyanates corresponding structurally to the formula (I) as set forth in claim 1 comprising reacting compounds conforming structurally to the formula (II)

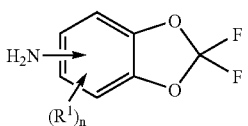

wherein R$^1$ and n are defined as in claim 1,
with thiocarbamic acid derivatives.

6. The process according to claim 5, wherein said thiocarbamic acid derivatives are selected from the group consisting of chlorothiocarbonylimidazole or thiocarbonylbisimidazole.

7. A process for preparing isothiocyanates corresponding structurally to the formula (I) as set forth in claim 1 comprising reacting compounds conforming structurally to the formula (II)

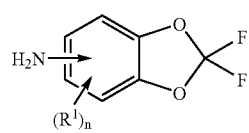

wherein R$^1$ and n are defined as in claim 1,
first with carbon disulphide in the presence of an alkali base and subsequently with an oxidizing agent.

8. A process for preparing isothiocyanates corresponding structurally to the formula (I) as set forth in claim 1 comprising reacting compounds conforming structurally to the formula (II)

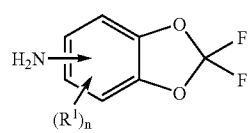

wherein R$^1$ and n are defined as in claim 1,
first with carbon disulphide in the presence of an alkali base and subsequently with phosgene.

9. A process for preparing isothiocyanates corresponding structurally to the formula (I) as set forth in claim 1 comprising reacting compounds conforming structurally to the formula (II)

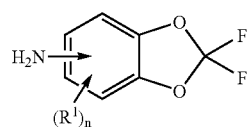

wherein R$^1$ and n are defined as in claim 1,
first with carbon disulphide in the presence of an alkali base and subsequently with oxalyl chloride.

* * * * *